United States Patent [19]

Schwing

[11] 4,049,705
[45] Sept. 20, 1977

[54] 2-ALKYL-1-NAPHTHOL-4-SULFONIC ACIDS

[75] Inventor: Gregory Wayne Schwing, Wilmington, Del.

[73] Assignee: E. I. Du Pont de Nemours and Company, Wilmington, Del.

[21] Appl. No.: 672,724

[22] Filed: Apr. 1, 1976

[51] Int. Cl.² .......................................... C07C 143/30
[52] U.S. Cl. .......................... 260/512 C; 260/543 H; 260/622 R
[58] Field of Search ........................ 260/512 C, 512 R

[56]  References Cited
U.S. PATENT DOCUMENTS 2,553,647   5/1951   Fieser et al. ........................ 260/396
2,872,368   2/1959   Sanders et al. ....................... 424/354

Primary Examiner—James O. Thomas, Jr.
Assistant Examiner—James H. Reamer

[57]  ABSTRACT

Compounds of the formula

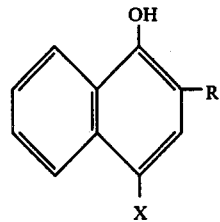

wherein R is alkyl of 11 to 14 carbon atoms, and
X is —SO₃H, —NO₂ or —SO₂Cl are useful intermediates in the preparation of naphthoquinone miticides.

2 Claims, No Drawings

2-ALKYL-1-NAPHTHOL-4-SULFONIC ACIDS

BACKGROUND OF THE INVENTION

This invention relates to 2-alkyl-1-naphthol derivatives which are useful in the preparation of naphthoquinone miticides. The miticides are known compounds described in German Pat. application No. 2,520,739. The compounds of this invention provide an economical route to the synthesis of the miticides which were previously synthesized by a completely different and less efficient process. See U.S. Pat. Nos. 2,553,647 and 2,553,648.

Salts of alkyl naphthol sulfonic acid have been mentioned in the art. U.S. Pat. No. 2,872,368 describes compounds of the formula

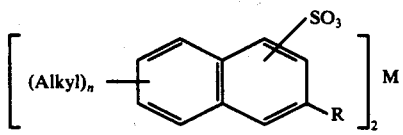

wherein

M is calcium or magnesium,

R is hydrogen, methyl or hydroxyl, and (Alkyl)$_n$ is 1-3 alkyl radicals containing 8-18 carbon atoms.

This patent describes no specific isomers and does not provide any method for preparation of these compounds.

SUMMARY OF THE INVENTION

Compounds of the formula

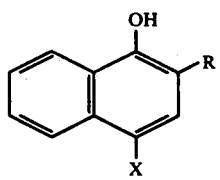

wherein

R is alkyl of 11 to 14 carbon atoms, and

X is —NO$_2$, —SO$_3$H or —SO$_2$Cl are novel compounds useful as intermediates in the preparation of naphthoquinone miticides. Because the most active of the miticides is the dodecyl substituted naphthoquinone, the compounds of the above formula where R is alkyl of 12 carbon atoms are preferred. Preferred for their ease of synthesis are compounds of the above formula where X is —SO$_3$H or —SO$_2$Cl. Most preferred is 2-dodecyl-1-naphthol-4-sulfonic acid.

DETAILED DESCRIPTION OF THE INVENTION

The preparation of the compounds of this invention begins with an appropriate 2-higher alkyl-1-naphthol, which can be prepared by the methods taught by K. Nakanishi and L. F. Fieser, J. Amer. Chem. Soc., 74, 3910 (1952) and G. Fawaz and L. F. Fieser, J. Amer. Chem. Soc., 72, 996 (1950). The reaction of an appropriate 2-higher alkyl-1-naphthol with sulfuric acid, chlorosulfonic acid, or nitric acid at 25° over a period of several minutes to one hour affords the corresponding sulfonic acid, sulfonyl chloride, or nitro compound.

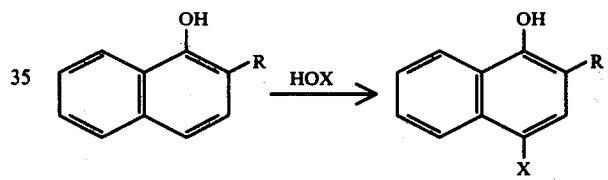

where R is alkyl of 11 to 14 carbon atoms and X is —SO$_3$H, —SO$_2$Cl, or —NO$_2$. The molar ratio of the 2-higher alkyl-1-naphthol to the acid HOX is preferably in the range of 1:1 to 1:3. Generally, an excess of the acid is employed to obtain higher yields of the desired product. The reactions are most conveniently run at ambient temperature over a period of a few minutes to 1 hour. However, the reaction mixture may be heated to hasten the rate of reaction or cooled to moderate the rate of reaction. The reactions can be run without solvent; or, an inert organic solvent such as dichloromethane, ether, chlorobenzene, acetic acid, or chloroform can be employed to obtain a homogeneous reaction mixture or so that the product precipitates from the reaction mixture.

The compounds of this invention can be used to prepare 2-higher alkyl-3-hydroxy-1,4-naphthoquinone carboxylic acid esters by the following representative procedure:

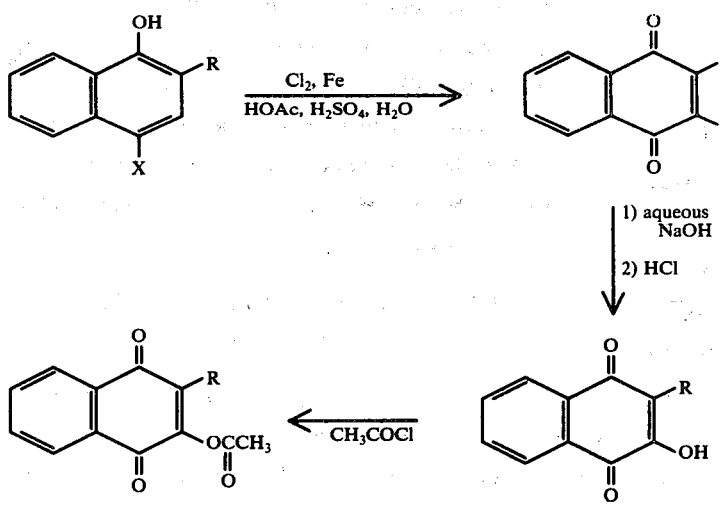

The naphthoquinone compounds of the formula

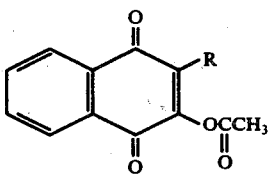

and their use as miticides in agriculture are described in German Pat. application No. 2,520,739. Of these compounds, the compound where R is dodecyl is preferred.

The following examples further illustrate this invention. All parts are by weight and temperatures are in degrees centigrade.

EXAMPLE 1

Preparation of 2-n-Dodecyl-1-naphthol-4-sulfonic Acid

A solution of 90 parts of sulfuric acid and 670 parts of dichloromethane was added in one portion to a solution of 100 parts of 2-n-dodecyl-1-naphthol and 670 parts of dichloromethane at ambient temperature. After 10 minutes, the mixture was filtered and the precipitate was washed three times with 670 parts of dichloromethane and dried to yield 111 parts of 2-n-dodecyl-1-naphthol-4-sulfonic acid, m.p. 127°–130° C.

EXAMPLE 2

Preparation of 2-n-Dodecyl-1-naphthol-4-sulfonyl Chloride

A solution of 18 parts of chlorosulfonic acid in 67 parts of dichloromethane was added to a solution of 7 parts of 2-n-dodecyl-1-naphthol in 67 parts of dichloromethane in one portion at ambient temperature. The resulting mixture was refluxed for 5 minutes, permitted to stand for 1 hour, and then poured into 100 parts of ice water. The dichloromethane was separated, washed with two 100-part portions of brine, dried with anhydrous magnesium sulfate and evaporated to afford 5 parts of the oily 2-n-dodecyl-1-naphthol-4-sulfonyl chloride, $n_D^{25} = 1.556$.

EXAMPLE 3

Preparation of 2-n-Dodecyl-4-nitro-1-naphthol

To a solution of 50 parts of 2-n-dodecyl-1-naphthol in 500 parts of glacial acetic acid was added 28 parts of nitric acid (specific gravity 1.4). The solution was stirred at ambient temperature for 1 hour and then poured into 2,000 parts of water. The resulting mixture was extracted with 1,400 parts of ether. The ether layer was separated; washed once with water (2,000 parts), twice with 10% aqueous sodium bicarbonate solution (2,000 parts), and finally with water (2,000 parts). The ether solution was dried with anhydrous magnesium sulfate and evaporated to afford 56 parts of 2-n-dodecyl-4-nitro-1-naphthol as a viscous yellow oil, $n_D^{25} = 1.5454$, which slowly crystallized to a waxy yellow solid on standing.

By the general procedures of Examples 1, 2 or 3, the following compounds can be prepared:
2-n-undecyl-1-naphthol-4-sulfonic acid
2-n-tridecyl-1-naphthol-4-sulfonic acid
2-n-tetradecyl-1-naphthol-4-sulfonic acid
2-n-undecyl-4-nitro-1-naphthol
2-n-tridecyl-4-nitro-1-naphthol
2-n-tetradecyl-4-nitro-1-naphthol
2-n-undecyl-1-naphthol-4-sulfonyl chloride
2-n-tridecyl-1-naphthol-4-sulfonyl chloride
2-n-tetradecyl-1-naphthol-4-sulfonyl chloride

EXAMPLE 4

Use of 2-n-Dodecyl-1-naphthol-4-sulfonic Acid in the Preparation of
3-Acetoxy-2-n-dodecyl-1,4-naphthoquinone A. Preparation of
3-Chloro-2-n-dodecyl-1,4-naphthoquinone A mixture of 6.3 parts of 2-n-dodecyl-1-naphthol-4-sulfonic acid, 100 parts of acetic acid, 18 parts of water, 21 parts of sulfuric acid, and 1 part of ferric chloride hexahydrate was cooled to 20°. Chlorine (3.1 parts) was added to this mixture with vigorous stirring. The temperature rose to 35° and the mixture turned yellow. The mixture was heated to 95° over 15 minutes and the temperature of the reaction mixture was maintained at 95° to 100° for 1 hour. Thirty parts of water were added and the mixture was then cooled to 25° with vigorous stirring. The crude product, which separated as brown granules, was filtered off and washed three times with water (25 parts), twice with 10% aqueous sodium bicarbonate (25 parts), twice with water (25 parts), twice with cold ethanol (8 parts), and twice with cold hexane (7 parts), to afford 5 parts of 3-chloro-2-n-dodecyl-1,4-naphthoquinone, m.p. 85°–87° C.

B. Preparation of 2-n-Dodecyl-3-hydroxy-1,4-naphthoquinone

A mixture of 10 parts of 3-chloro-2-n-dodecyl-1,4-naphthoquinone. 5-parts of 50% aqueous sodium hydroxide and 320 parts of 95% aqueous ethanol were heated at reflux for 15 minutes. The color of the mixture turned from yellow to dark red. The mixture was cooled to 25° and acidified with 10% aqueous hydrochloric acid. The color of the mixture was golden yellow after acidification. The product was filtered off and washed twice with water (25 parts) and twice with cold methanol (25 parts) to yield 8 parts of 2-n-dodecyl-3-hydroxy-1,4-naphthoquinone, mp. 85° – 87° C.

C. Preparation of 2-Acetoxy-2-n-dodecyl-1,4-naphthoquinone

A mixture of 2.0 parts of 2-n-dodecyl-3-hydroxyl-1,4-naphthoquinone, 0.81 parts of triethylamine, 0.63 parts of acetyl chloride and 50 parts of methylene chloride was stirred at room temperature for 30 hours. The resulting mixture was distributed between methylene chloride and water. The methylene chloride layer was separated, dried over magnesium sulfate, then filtered and evaporated under reduced pressure. The residue was crystallized from petroleum ether (b.p. 30°–60° C) to give 1.2 parts of 3-acetoxy-2-n-dodecyl-1,4-naphthoquinone, m.p. 57°–58° C.

I claim:
1. A compound of the formula

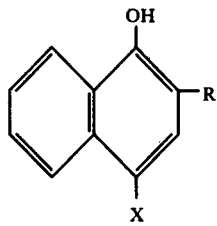

wherein
R is alkyl of 11 to 14 carbon atoms, and
X is —$SO_3H$.
2. A compound of claim 1 wherein R is alkyl of 12 carbons.

* * * * *